(12) United States Patent
Oh et al.

(10) Patent No.: US 6,300,489 B1
(45) Date of Patent: *Oct. 9, 2001

(54) SMALL AND CYSTEINE RICH ANTIFUNGAL DEFENSIN AND THIONINE-LIKE PROTEIN GENES HIGHLY EXPRESSED IN THE INCOMPATIBLE INTERACTION

(75) Inventors: Boung-Jun Oh; Moon Kyung Ko; Byongchul Shin, all of Kwangju (KR)

(73) Assignee: Korea Kumho Petrochemical Co., Ltd., Seoul (KR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/442,631

(22) Filed: Nov. 18, 1999

(51) Int. Cl.[7] .............................. C07H 21/04; C07H 21/02
(52) U.S. Cl. ...................... 536/23.6; 536/23.1; 436/94; 435/69.1; 435/410; 435/468.1; 435/320.1; 800/279; 800/295; 800/307
(58) Field of Search ................................. 536/23.1, 23.6; 436/94; 435/69.1, 410, 468.1, 320.1; 800/205, 279, 307

(56) References Cited

U.S. PATENT DOCUMENTS 5,608,144 * 3/1997 Baden et al. .................. 800/205

OTHER PUBLICATIONS

Oh et al. Coexpression of a defensin gene and thionin-like gene via differential signal transduction pathways in pepper and colletotrichum gloeosporiodes interactions. Plant Molecular Biology 41(3):313–319, Oct. 1999.*

Epple et al., An Arabidopsis thaliana Thionin Gene Is Inducible via a Signal Transduction Pathway Different from That for Pathogenesis–Related Proteins, Plant Physiol., 1995, 109:813–820.

Terras et al., Small Cysteine–Rich Antifungal Proteins from Radish: Their Role in Host Defense, The Plant Cell, 1995, 7:573–588.

Heck & Ho, Gibberellin–repressible gene expression in the barley aleurone layer, Plant Molecular Biology, 1996, 30:611–623.

Ebrahim–Nesbat et al., Cultivar–related differences in the distribution of cell–wall–bound thionins in compatible and incompatible interactions between barley and powdery mildew, Planta, 1989, 179:203–210.

Penninckx et al., Pathogen–induced Systemic Activation of a Plant Defensin Gene in Arabidopsis Follows a Salicylic Acid–Independent Pathway, The Plant Cell, 1996, 8:2309–2323.

Salzman et al., Coordinate Accumulation of Antifungal Proteins and Hexoses Consitutes a Developmentally Controlled Defense Response during Fruit Ripening in Grape, Plant Physiol., 1998, 117:465–472.

Manandhar et al., Anthraenose Development on Pepper Fruits Inoculated with *Coletotrichum gloeosporioides*, Plant Disease, 1995, 79(4):380–383.

Bohlmann et al., Leaf–specific thionins of barley—a novel class of cell wall proteins toxic to plant–pathogenic fungi and possible involved in the defence mechanism of plants, The EMBO Journal, 1988, 7(6):1559–1565.

* cited by examiner

*Primary Examiner*—Christopher S. F. Low
*Assistant Examiner*—Stephen Tu
(74) *Attorney, Agent, or Firm*—Kenyon & Kenyon (57) ABSTRACT

The present invention related to two cDNA clones, designated to PepDef (pepper defensin protein gene) and PepThi (pepper thionin-like protein gene) and individual component; thereof including its coding region and its gene product; modification thereto; application of said gene, coding region and modification thereto; DNA construct, vectors and transformed plants each comprising the gene or part thereof.

1 Claim, 4 Drawing Sheets

SEQUENCE LISTING

<160> NUMBER OF SEQ ID NOS: 4

<210> SEQ ID NO 1
<211> LENGTH: 506
<212> TYPE: DNA
<213> ORGANISM: Capsicum annuum

<400> SEQUENCE: 1

```
aaagagacta tggctcgttc catttacttc atggcatttc ttgtcttggc aatgacactc        60
tttgttgctt atggggtgca aggcaaggaa atttgctgta aagagctcac aaaacctgtt       120
aaatgttcta gtgaccctct atgtcaaaaa ctctgtatgg agaaggagaa atatgaagat       180
ggtcattgtt tcacaatcct aagcaagtgc ttatgcatga agagatgtaa tgctaaaact       240
ctcgcaacag aattgcttgc ttgaagaaga gttcctcaag cagtaattaa gtttgattat       300
ggatttagtg tcacacaaaa ttaaataaag tgttgccttt cttaaaaggg taacttataa       360
tgttgtattc ttggtgtata gtagccattt gacacattaa attaaagttg tgacacatca       420
atccttcatg tatcttctat taagtttgtg tgtttttaatg aaaagagatc gtttacggtc       480
taaaaaaaaa aaaaaaaaaa aaaaaa                                             506
```

<210> SEQ ID NO 2
<211> LENGTH: 83
<212> TYPE: PRT
<213> ORGANISM: Capsicum annuum

<400> SEQUENCE: 2

```
Met Ala Arg Ser Ile Tyr Phe Met Ala Phe Leu Val Leu Ala Thr Leu
  1               5                  10                  15

Phe Val Ala Tyr Gly Val Gln Gly Lys Glu Ile Cys Cys Lys Glu Leu
             20                  25                  30

Thr Lys Pro Val Lys Cys Ser Ser Asp Pro Leu Cys Gln Lys Leu Cys
         35                  40                  45

Met Glu Lys Glu Lys Tyr Glu Asp Gly His Cys Phe Thr Ile Leu Ser
     50                  55                  60
```

```
Lys Cys Leu Cys Met Lys Arg Cys Asn Ala Lys Thr Leu Ala Thr Glu
 65                  70                  75                  80

Leu Leu Ala

<210> SEQ ID NO 3
<211> LENGTH: 225
<212> TYPE: DNA
<213> ORGANISM: Capsicum annuum

<400> SEQUENCE: 3
atggctggct tttccaaagt ggttgcaact attttctta tgatgttgct ggtttttgct     60
actgatatga tggcggaggc aaagatctgc gaggcgttga gcggcaactt caaggggttg    120
tgccttagta gccgcgattg tggtaatgtt tgccgtagag agggatttac cgatggctct    180
tgcattggat tccgtcttca atgcttctgc acgaagccct gtgct                    225

<210> SEQ ID NO 4
<211> LENGTH: 74
<212> TYPE: PRT
<213> ORGANISM: Capsicum annuum

<400> SEQUENCE: 4

Met Ala Gly Phe Ser Lys Val Val Ala Thr Ile Phe Leu Met Met Lys
 1               5                  10                  15

Val Phe Ala Thr Asp Met Met Ala Glu Ala Lys Ile Cys Glu Ala Leu
                 20                  25                  30

Ser Gly Asn Phe Lys Gly Leu Cys Leu Ser Ser Arg Asp Cys Gly Asn
             35                  40                  45

Val Cys Arg Arg Glu Gly Phe Thr Asp Gly Ser Cys Ile Gly Phe Arg
         50                  55                  60

Leu Gln Cys Phe Cys Thr Lys Pro Cys Ala
 65                  70
```

SMALL AND CYSTEINE RICH ANTIFUNGAL DEFENSIN AND THIONINE-LIKE PROTEIN GENES HIGHLY EXPRESSED IN THE INCOMPATIBLE INTERACTION

BACKGROUND OF THE INVENTION

The present invention related to two cDNA clones, designated to PepDef (pepper defensin protein gene) and PepThi (pepper thionin-like protein gene) and individual component; thereof including its coding region and its gene product; modification thereto; application of said gene, coding region and modification thereto; DNA construct, vectors and transformed plants each comprising the gene or part thereof.

Plants have developed defense mechanisms to defend themselves against phytopathogens. Plants' first responses to pathogen infection include fortification of cell walls for physical barriers by deposition of lignin (Dean and Kúc, 1988) and by oxidative cross-linking (Brisson et al., 1994) as well as the hypersensitive reaction (HR). HR causes a rapid cell death of infected tissues to halt further colonization by pathogens (Goodman and Novacky, 1994). The next array of defense strategies includes the production of antimicrobial phytoalexins (van Etten et al., 1989), pathogenesis-related (PR) proteins (Linthorst, 1991; Ponstein et al., 1994), and cysteine (Cys)-rich proteins, such as lipid transfer protein (Garcia-Olmedo et al., 1995) and thionins (Bohlmann, 1994).

Thionins are small, highly basic, Cys-rich proteins that show antimicrobial activity and seem to have a role in plant defense against fungi and bacteria. The overexpression of the THI2.1 thionin in Arabidopsis enhanced resistance to a phytopathogenic fungus (Epple et al., 1997). The overexpression of α-hordothionin in tobacco also enhanced resistance to a phytopathogenic bacterium (Carmona et al., 1993). In addition, during barley and powdery mildew interactions, the accumulation of thionins was higher in the incompatible interaction than in the compatible one (Ebrahim-Nesbat et al., 1993).

The thionins contain a signal sequence, the thionin domain and an acid polypeptide domain as well as the conserved Cys residues (Bohlmann et al., 1994). A new class of Cys-rich antimicrobial protein, γ-thionin, has a similar size (5 kD) and the same number of disulfide bridges as thionins. However, since γ-thionins do not have significant sequence homologies with thionins, they have been described as plant defensins (Terras et al., 1995). Both defensin and thionin genes in Arabidopsis are inducible via a salicylic acid-independent pathway different from that for PR proteins (Epple et al., 1995; Penninckx et al., 1996).

Fruit ripening represents a genetically synchronized process that involves developmental events unique to plant species. Generally, ripe fruits are susceptible to pathogen attack (Swinburne, 1983; Prusky et al., 1991). Therefore, fruit as one of the reproductive organs of the plants must be protected from pathogens to maintain their integrity and seed maturation. Several antifungal proteins that are responsible for protection against pathogens during fruit ripening have been identified (Fils-Lycaon et al., 1996; Meyer et al., 1996; Salzman et al., 1998). Also, PR proteins are developmentally expressed during the formation of flowers (Lotan et al., 1989; Cote et al., 1991).

*Colletotrichum gloeosporioides* (Penz.) causes anthracnose diseases in many plant species (Daykin, 1984; Dodds et al., 1991; Prusky et al., 1991). *C. gloeosporioides* is the most prevalent species among *C. acutatum, C. coccodes, C. dematium, C. gloeosporioides,* and *G. cingulata* to cause anthracnose diseases on pepper (*Capsicum annuum* L.) (Kim et al., 1986; Manandhar et al., 1995). In previous study, we found that the unripe-mature-green fruit of pepper cv. Nokkwang interacted compatibly with *C. gloeosporioides,* whereas the interaction of the ripe-red fruits with fungus was incompatible (Oh et al., 1998). To investigate the activation of defense-related genes from the incompatible-pepper fruit upon *C. gloeosporioides* infection, we isolated a defensin gene and a thionin-like gene by using mRNA differential display. The regulation of these Cys-rich protein genes was studied during fruit ripening and in the initial infection process during the compatible and incompatible interactions. We report here what appears to be the first case of a defensin gene and a thionin-like gene induced via different signal transduction pathways in a plant and fungus interaction.

SUMMARY OF THE INVENTION

The present invention relates to two cDNA clones, designated to a defensin gene, PepDef, and a thionin-like gene, PepThi, the sequences of which are depicted in SEQ ID No. 1 and No. 3, respectively. The anthracnose fungus, *C. gloeosporioides,* interacts incompatibly with ripe fruits of pepper (*Capsicum annuum*). It interacts compatibly with the unripe-mature fruits. We isolated PepDef and PepThi expressed in the incompatible interaction by using mRNA differential display method. Both genes were developmentally regulated during fruit ripening, organ-specifically regulated, and differentially induced during the compatible and incompatible interactions. The expression of PepThi gene was rapidly induced in the incompatible-ripe fruit upon fungal infection. The fungal-inducible PepThi gene is highly inducible only in the unripe fruit by salicylic acid. In both ripe and unripe fruits, it was induced by wounding, but not by jasmonic acid. The expression of PepDef gene is enhanced in the unripe fruit by jasmonic acid, while suppressed in the ripe fruit. These results suggest that both small and cysteine-rich protein genes are induced via different signal transduction pathways during fruit ripening to protect the reproductive organs against biotic and abiotic stresses. The PepDef and PepThi can be cloned into an expression vector to produce a recombinant DNA expression system suitable for insertion into cells to form a transgenic plant transformed with these genes. In addition, the PepDef and PepThi genes of this invention can be also used to produce transgenic plants that exhibit enhanced resistance against phytopathogens, including fungi, bacteria, viruses, nematode, mycoplasmalike organisms, parasitic higher plants, flagellate protozoa, and insects.

DETAILED DESCRIPTION OF THE INVENTION

The present invention has identified two cDNA clones, designated to PepDef and PepThi, from the incompatible interaction between pepper and the pepper anthracnose fungus *Colletotrichum gloeosporioides* using mRNA differential display and cDNA library screening.

Figure 1:
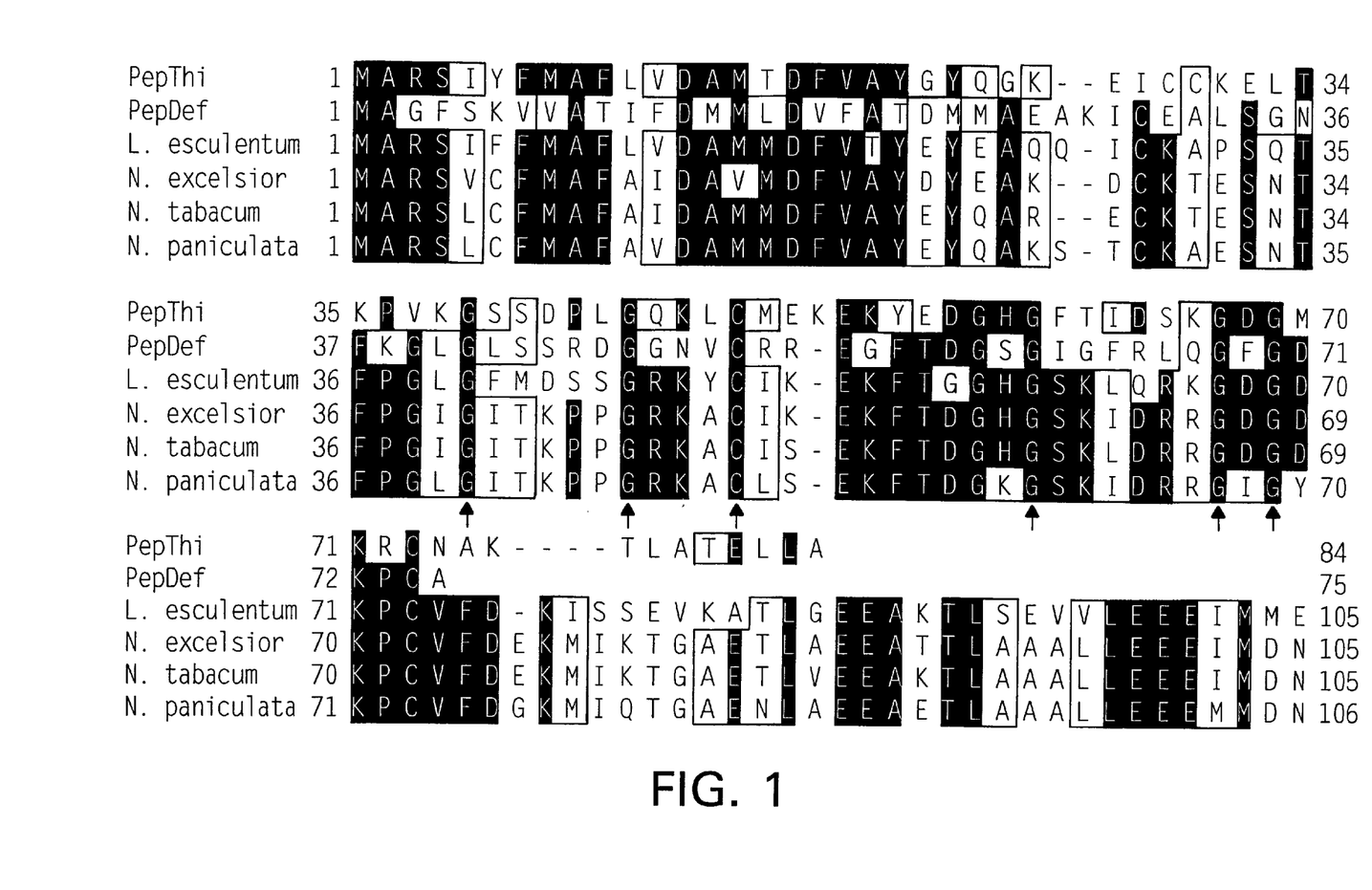
FIG. 1. Alignment of the deduced amino acid sequences from PepDef (GenBank accession number X95363) and PepThi cDNAs (AF112443) of pepper (Meyer et al., 1996) with other thionins from tomato (*Lycopersicon esculentum,* U20591; Milligan and Gasser, 1995), *Nicotiana excelsior* (AB005266), tobacco (*N. tabacum,* Z11748; Gu et al., 1992), and *N. paniculata* (AB005250). The conserved cysteine arrangement -C( . . . )C-X-X-X-C( . . . )G-X-C( . . . ) C-X-C- is indicated by arrows.

The PepThi cDNA is 506 bp in length with 9 bp of 5'-untranslated region and 245 bp of 3'-untranslated region including the poly(A) tail (GenBank AF112443). The PepThi clone represented a full-length cDNA of the 0.5 kb transcript identified by RNA gel blot analysis. The cDNA contained one open reading frame encoding a polypeptide of 9.5 kDa with 84 amino acids. The deduced amino acid sequence of PepThi(SEQ ID No. 4) contained an N-terminal secretory signal peptide that was cleaved after glycine at position 25 (FIG. 1). PepThi is a Cys-rich polypeptide containing the consensus Cys arrangement -C( . . . )C-X-X-X-C( . . . )G-X-C( . . . )C-X-C-.

The PepDef cDNA is 225 bp except 5'-untranslated region and 3'-untranslated region including the poly(A) tail (X95363). The PepDef clone represented a full-length cDNA of the 0.45 kb transcript identified by RNA gel blot analysis. The cDNA contained one open reading frame encoding a polypeptide of 8.5 kDa with 75 amino acids. The deduced amino acid sequence of PepDef(SEQ ID No. 3) contained an N-terminal secretory signal peptide that was cleaved after alanine at position 27 (FIG. 1). PepDef is also a Cys-rich polypeptide containing the consensus Cys arrangement-C( . . . )C-X-X-X-C( . . . )G-X-C( . . . )C-X-C-.

The expression of PepThi gene was observed in ripe fruits, leaves, stems, and roots of pepper, respectively. The basal and non-induced level of PepThi gene was higher in the leaves and roots than in the fruits and stems. In the fruits, the PepThi mRNA was highly induced by fungal infection and wounding. Also, the accumulation of the PepThi mRNA increased in the stems with fungal infection and wounding. However, the level of PepThi mRNA was not significantly changed in the leaves and roots by the treatments.

The PepDef mRNA was not detected in leaves, stems, and roots even after fungal infection and wounding. However, the basal level of PepDef gene was very high in the ripe fruit, and undetectably low in the unripe fruit. Interestingly, the level of PepDef mRNA was reduced in the ripe fruit by fungal infection and wounding. This phenomenon was also observed in the ripe fruit by JA treatment. The accumulation of PepDef mRNA was not significantly induced in the unripe fruit by fungal infection and wounding for 24 h or 48 h. These results suggest that PepDef and PepThi genes are developmentally and organ-specifically regulated, and the induction by fungal infection and wounding is also subject to developmental regulation.

To examine the time course of the induction of PepDef or PepThi mRNAs in response to the fungal infection, RNA gel blot analysis was performed with the ripe and unripe fruits at 0, 3, 6, 12, 24, 48, and 72 h after inoculation (HAI) using PepDef and PepThi cDNAs as probes. The uninoculated incompatible-ripe fruit contained a basal level of PepThi mRNA. However, the expression of PepThi was rapidly induced in the ripe fruit upon fungal infection and reached a maximum at 48 and 72 HAIs. In compatible-unripe fruits, the accumulation of PepThi mRNA was late, at 12 HAI, and reached its maximum level at 72 HAI.

Accumulation of PepDef mRNA in the unripe fruit was very low. PepDef expression was suppressed by fungal infection in the ripe fruit. The transcript levels dropped until 48 HAI, and had begun to increase again 72 HAI. Since PepDef gene was highly expressed in the ripe fruit and PepThi gene was induced in the ripe fruit by the fungal infection, these genes may be involved in the defense mechanism during fruit ripening against the phytopathogen.

Figure 4:
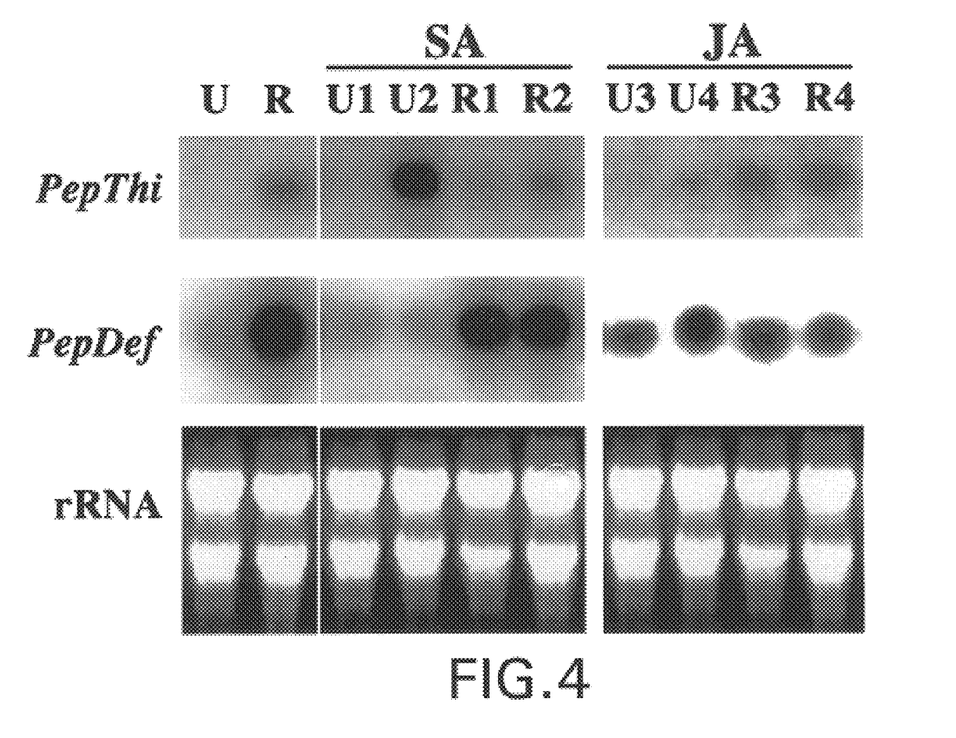
FIG. 4. Induction and suppression of PepDef and PepThi genes from both ripe and unripe fruits of pepper by exogenous salicylic acid (SA) and jasmonic acid (JA) treatments. RNAs were isolated from both ripe (R) and unripe fruits (U) treated with SA (1=0.5 mM, 2=5 mM) and JA (3=4 µM, 4=40 µM) for 24 h. Fruits treated with 10 µl sterile-water except fungal spores for 24 h were used as the control (C).

To identify inducers of PepDef and PepThi gene expression from fruits, RNA gel blot analysis was performed with unripe and ripe fruits treated with exogenous jasmonic acid (JA) and salicylic acid (SA) for 24 h. The PepThi mRNA was highly accumulated in the unripe fruit compared to in the ripe fruit by SA at 5 mM (FIG. 4). However, JA could not significantly induce the PepThi mRNA in both ripe and unripe fruits. The expression level of PepDef mRNA was not changed in both ripe and unripe fruits by SA. Interestingly, the expression of PepDef mRNA by JA increased in the unripe fruit, but decreased slightly in the ripe fruit. Taken together, these results suggest that the PepThi and PepDef genes are expressed via different signal transduction pathways during ripening.

The PepDef and PepThi genes can be cloned into an expression vector to produce a recombinant DNA expression system suitable for insertion into cells to form a transgenic plant transformed with these genes. In addition, the PepDef and PepThi genes of this invention can be also used to produce transgenic plants that exhibit enhanced resistance against phytopathogens, including fungi, bacteria, viruses, nematode, mycoplasmalike organisms, parasitic higher plants, flagellate protozoa, and insects.

EXAMPLES

Fungal Inoculum and Plant Material

Monoconidial isolate KG13 of *C. gloeosporioides* was cultured on potato dextrose agar (Difco, USA) for 5 days in darkness at 27° C. Sterile distilled water was added and conidia were harvested through four layers of cheesecloth to remove mycelial debris. Ten µl at 5×10$^5$ conidia/ml of *C. gloeosporioides* was used for the inoculation of both unripe and ripe pepper fruit as described (Oh et al., 1998).

Both ripe-red and unripe-mature-green fruits of pepper cv. Nokkwang were grown and harvested under green-house conditions. For wound treatments, five healthy ripe and unripe fruits were deeply scratched by a knife and incubated under relative humidity of 100% at 27° C. in the dark. Ten µl of SA (0.5 and 5 mM) and JA (4 and 40 µM) was applied to both ripe and unripe sets of five fruits. After incubation under the condition described above, the fruits were excised to 1 cm$^2$ at the application site and frozen in liquid nitrogen.

Leaf, root, and stem samples were harvested from 3-week-old plants and handled as described above for fungal inoculation and wounding.

mRNA Differential Display

Total RNA was extracted from healthy and infected ripe and unripe fruits using RNeasy Plant kit (Qiagen, Germany) according to the manufacturer's instruction. We used total RNA as template for the reverse transcriptase reaction and performed differential display with [$\alpha^{33}$P]dATP instead of [$\alpha^{35}$S]dATP (Liang and Pardee, 1992). Anchored primers and random-arbitrary primers were purchased from Operon Technologies (Alameda, Calif., USA). PCR-amplified cDNA fragments were separated on denaturing 5% polyacrylamide gels in Tris-borate buffer. cDNAs were recovered from the gel, amplified by PCR, and cloned into pGEM-T easy vector (Promega, USA) as described (Oh et al., 1995).

Construction and Screening of cDNA Library

Poly(A)$^+$mRNA was purified from total RNA of unripe fruits at 24 and 48 h after inoculation with C. goeosporioides using Oligotex mRNA Kit (Qiagen, Germany). The cDNA library (2.5×10$^5$ plaque-forming unit with the mean insert size of 1.2 kb) was constructed in the cloning vector $\mu$ZAPII (Stratagene, Germany) according to the manufacturer's instruction.

A partial cDNA, designated pddThi, from the differential display was used as a probe to screen the C. gloeoporioides-induced pepper cDNA library. After three rounds of plaque hybridization, positive plaques were purified. The pBluescript SK phagemid containing cDNAs was excised in vivo from the ZAP Express vector using the ExAssit helper phage.

DNA Sequencing and Homology Search

The cDNA sequencing was performed with an ALFexpress automated DNA sequencer (Pharmacia, Sweden). Analysis of nucleotide and amino acid sequences was performed using the DNASIS sequence analysis software for Windows, version 2.1 (Hitachi, Japan). The multiple sequence alignment was produced with the Clustal W program. For a homology search, cDNA sequence was compared to the NCBI non-redundant databases using the BLAST electronic mail server (Altschul et al., 1997).

RNA Blot and Hybridization

Total RNA (10 $\mu$g/lane) from each plant tissue used in this study was separated on 1.2% denaturing agarose gels in the presence of formaldehyde. RNA gel-blotting, hybridization and washing were conducted as described by the manufacturer of the positively charged nylon membrane employed (Hybond N$^+$; Amersham, UK). Radiolabeled probes were prepared with [$\alpha^{32}$P]dCTP (Amersham) using a random primer-labeling kit (Boehringer Mannheim, Germany).

Cloning and Characterization of Thionin-like cDNAs

C. gloeosporioides showed the incompatible interaction with ripe-red fruits of pepper and the compatible interaction with unripe-mature-green fruits (Oh et al., 1998). We isolated several cDNAs induced from the ripe fruit, but not from the unripe fruit by the fungal infection using mRNA differential display. By nucleotide sequence analysis of cDNAs, two cDNA fragments were identified to be thionin homologs. One cDNA was full length and was similar to j1-1 cDNA that encodes a fruit specific defensin (Meyer et al., 1996). We named the defensin as PepDef (pepper defensin). Another cDNA fragment, designated pddThi, showed homology to $\gamma$-thionin from tobacco (Gu et al., 1992). In preliminary RNA gel blot analysis, the two mRNAs accumulated to high levels in the incompatible interaction. A full-length cDNA clone of pddThi was isolated from a cDNA library prepared from pepper fruits 24 and 48 h after inoculation with the fungus. The full-length clone was designated pPepThi (paper thionin) and sequenced.

The pPepThi cDNA is 506 bp in length with 9 bp of 5'-untranslated region and 245 bp of 3'-untranslated region including the poly(A) tail (GenBank AF112443). The pPepThi clone represented a full-length cDNA of the 0.5 kb transcript identified by RNA gel blot analysis. The cDNA contained one open reading frame encoding a polypeptide of 9.5 kDa with 84 amino acids. The deduced amino acid sequence of PepThi contained an N-terminal secretory signal peptide that was cleaved after glycine at position 25 (FIG. 1). PepThi is a Cys-rich polypeptide containing the consensus Cys arrangement -C( . . . )C-X-X-X-C( . . . ) G-X-C( . . . )C-X-C-.

A sequence alignment showed that the PepThi shared significant homology (identity and similarity: 50% and 64%, respectively) to a flower-specific $\gamma$-thionin from tobacco (Gu et al., 1992) and to several other $\gamma$-thionins from Nicotiana species and tomato (Milligan and Gasser, 1995; FIG. 1). PepThi protein showed 29% identity for the whole coding region to a pepper defensin protein PepDef PepThi did not have nucleotide sequence homology to thionins and was different from other $\gamma$-thionins. Thus, we assigned PepThi as a thionin-like protein.

Expression Pattern and Induction by Fungal Infection and Wounding

Figure 2:
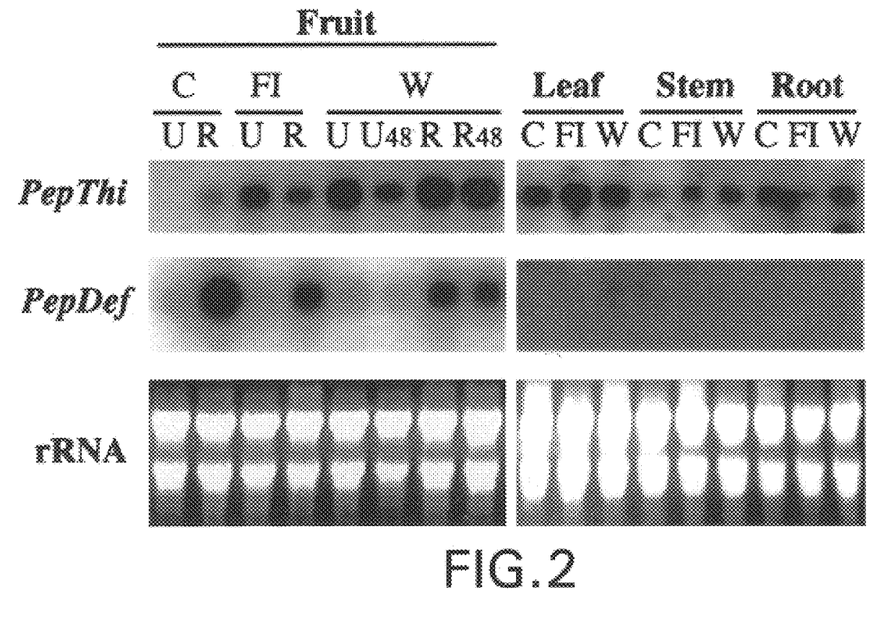
FIG. 2. Expression and induction of PepDef and PepThi genes from various organs of pepper by *Colletotrichum gloeosporioides* infections and wounding. RNAs were isolated from ripe fruit (R), unripe fruit (U), leaf, stem, and root at 24 h after the treatments of fungal infection (FI) and wounding (W). In addition, RNAs of both ripe and unripe fruits at 48 h after wounding (R48 and U48) were isolated. Ten µl at 5×10$^5$ conidia/ml of *C. gloeosporioides* was used for the inoculation of various pepper organs. Organs treated with 10 µl sterile-water except fungal spores for 24 h were used as the controls (C).

To examine the PepThi gene expression in various organs and its inducibility by fungal inoculation and wounding, RNA gel blot analysis was performed using total RNAs prepared from fruits, leaves, stems, and roots of pepper plants at 24 h after treatments. The expression of PepThi gene was observed in ripe fruits, leaves, stems, and roots (FIG. 2). The basal and non-induced level of PepThi gene was higher in the leaves and roots than in the fruits and stems. In the fruits, the Pepmhi mRNA was highly induced by fungal infection and wounding. Also, the accumulation of the PepThi mRNA increased in the stems with fungal infection and wounding. However, the level of PepThi mRNA was not significantly changed in the leaves and roots by the treatments.

We hybridized the PepDef cDNA to the same blot that was used for the hybridization of PepThi cDNA. The basal level of PepDef gene was very high in the ripe fruit, and undetectably low in the unripe fruit (FIG. 2). The PepDef mRNA was not detected in leaves, stems, and roots even after the treatments. PepDef protein is wound-inducible in the unripe fruit at 3 days after treatment (Meyer et al., 1996). However, the accumulation of PepDef mRNA was not significantly induced in the unripe fruit by fungal infection and wounding for 24 h or 48 h. Interestingly, the level of PepDef mRNA was reduced in the ripe fruit by fungal infection and wounding. These phenomena were also observed in the ripe fruit by fungal infection and JA treatment (see FIGS. 3 and 4). These results suggest that PepThi and PepDef genes are developmentally and organ-specifically regulated, and the induction by fungal infection and wounding is also subject to developmental regulation.

Differential Induction by Fungal Infection During Fruit Ripening

Figure 3:
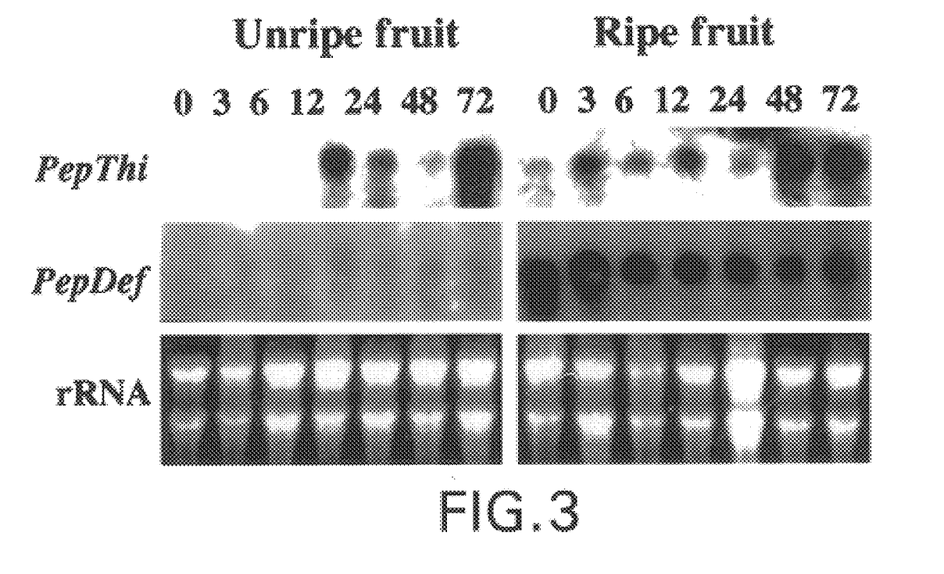
FIG. 3. Differential induction of PepDef and PepThi genes from both ripe and unripe fruits of pepper by *Colletotrichum gloeosporioides* infections. RNAs were isolated from both ripe (incompatible interaction) and unripe fruits (compatible interaction) after the fungal infection with time course. Time is indicated in h after infection.

In our previous study for fungal morphogenesis on the surface of fruits, conidial germination, initial and mature infection hypha were observed at 2, 12, and 24 h after inoculations (HAIs), respectively (Oh et al. 1998). The initial anthracnose symptoms were detected only on the unripe fruit at 2 days after inoculation, resulting in typical sunken necrosis within 5 days after inoculation. To examine the time course of the induction of PepThi or PepDef mRNAs in response to the fungal infection, RNA gel blot analysis was performed with the ripe and unripe fruits at 0, 3, 6, 12, 24, 48, and 72 HAI using PepThi and j1-1 cDNAs as probes. The uninoculated incompatible-ripe fruit contained a basal level of PepThi mRNA (FIGS. 2 and 3). However, the expression of PepThi was rapidly induced in the ripe fruit upon fungal infection and reached a maximum at 48 and 72 HAIs (FIG. 3). In compatible-unripe fruits, the accumulation of PepThi mRNA was late, at 12 HAI, and reached its maximum level at 72 HAI.

Accumulation of PepDef mRNA in the unripe fruit was very low (FIG. 3). As shown in FIG. 2, PepDef expression was suppressed by fungal infection in the ripe fruit. The transcript levels dropped until 48 HAI, and had begun to increase again 72 HAI. Since PepDef gene was highly expressed in the ripe fruit and PepThi gene was induced in the ripe fruit by the fungal infection, these genes may be involved in the defense mechanism during fruit ripening against the phytopathogen.

Induction and Suppression During Fruit Ripening by JA and SA

To identify the inducers of PepThi and PepDef gene expression from fruits, RNA gel blot analysis was performed with the unripe and ripe fruits treated with exogenous JA and SA for 24 h. The PepThi mRNA was highly accumulated in the unripe fruit compared to in the ripe fruit by SA at 5 mM (FIG. 4). However, JA could not significantly induce the PepThi mRNA in both ripe and unripe fruits. The expression level of PepDef mRNA was not changed in both ripe and unripe fruits by SA. Interestingly, the expression of PepDef mRNA by JA increased in the unripe fruit, but decreased slightly in the ripe fruit. Taken together, these results suggest that the PepThi and PepDef genes are expressed via different signal transduction pathways during ripening.

Discussion

Fungal-inducible thionin genes were identified in several plant/fungus interactions, such as in *Arabidopsis/Fusarium oxysporum* f.sp. *matthiolae* (Epple et al., 1995), barley/ *Stagonospora nodorum* (Titarenko et al., 1993; Stevens et al., 1996), and barley/the mildew fungus (Boyd et al., 1994; Bohlmann et al., 1998). Relevant to these findings, the accumulation of barley leaf thionin in papillae and in the cell wall surrounding the infection peg was higher in the incompatible interaction than that in the compatible one (Ebrahim-Nesbat et al., 1989, 1993). Similar phenomena have been reported for many other plant and pathogen interactions. The induction of PepThi mRNA was observed to be faster in the incompatible interaction of ripe pepper fruits with the fungus (FIG. 3).

The PepThi gene was induced during the early conidial germination of the fungus, before infection hyphae formation (Oh et al., 1998) and even before appressorium formation (Kim et al., 1999). These results suggest that signaling compounds released/produced during fungal germination result in the expression of PepThi gene in the epidermal cells of the incompatible-ripe fruit. Since the PepThi gene is expressed in various organs of pepper plants and its expression level is enhanced by fungal inoculation and wounding (FIG. 2), PepThi thionin-like protein could play a role in conferring systemic protection for the plants against both biotic and abiotic stresses. Also, the induction of PepThi gene in the unripe fruit by SA (FIG. 4) is consistent with a systemic protection role. SA plays an important role in the signal transduction pathway leading to the systemic acquired resistance (Gaffney et al., 1993).

The expression of the PepDef gene is regulated during fruit ripening. Similarly, several defensins and thionins are specifically expressed in reproductive organs, such as flowers in tobacco (Gu et al., 1992) and Arabidopsis (Epple et al., 1995), pistils in petunia (Karunanandaa et al., 1994), and seeds in radish (Terras et al., 1995). These findings suggest that both defensins and thionins are possibly involved in the defense mechanism for protecting the reproductive organ against pathogens or wounds. Further, thionins and other Cys-rich proteins exhibit synergistically enhanced antifungal activity (Terras et al., 1993). Therefore, the concerted expression of both PepDef and PepThi genes during ripening could confer disease resistance in the ripe fruit during the early fungal infection process.

The responses to exogenous JA and SA treatments in pepper during fruit ripening are different for both PepDef and PepThi genes. JA as a chemical elicitor induces thionin genes in Arabidopsis (Epple et al., 1995; Vignutelli et al., 1998) and barley (Andresen et al., 1992), and defensin genes in Arabidopsis (Penninckx et al., 1996), in addition to other wound inducible genes (Hildmann et al., 1992; Reinbothe et al., 1994). SA also induces a thionin gene in barley leaf (Kogel et al., 1995) as well as PR proteins (Ward et al., 1991; Uknes et al., 1992). A JA-independent wound induction pathway that shows opposite regulation to the JA-dependent one was identified in Arabidopsis (Rojo et al., 1998). In the present study, the PepThi gene is strongly inducible in the unripe fruit by SA and wounding, but not by JA (FIG. 4). These data indicate that the PepThi gene is expressed via a JA-independent wound signal transduction pathway.

Since the PepDef gene is induced in the unripe fruit by JA, it is probably regulated via the octadecanoid pathway (Peña-Cortés et al., 1995; Bergey et al., 1996). The slightly suppression of the PepDef gene in the ripe fruit by JA and wounding is puzzling, since both JA in the unripe fruit result in the induction of PepDef mRNA. The possible explanation is that JA may elicit other signals that are able to activate genes in response to JA. These additional signals may result in the inhibition of PepDef expression in the ripe fruit.

This present study shows that a defensin and a thionin-like protein that may have defensive roles are deployed via different signal transduction pathways and may protect pepper fruits against the anthracnose fungus.

REFERENCES

1. Altschul S F, Madden T L, Schäffer A A, Zhang J, Zhang Z, Miller W, Lipman D J: Gapped BLAST and PSI-BLAST: a new generation of protein database search programs. Nucleic Acids Res 25: 3389–3402 (1997).
2. Andresen I, Becker W, Schlüter K, Burges J, Parthier B, Apel K: The identification of leaf thionin as one of the main jasmonate-induced proteins of barley (Hordeum vulgare). Plant Mol Biol 19: 193–204 (1992).
3. Bergey D R, Howe G A, Ryan C A: Polypeptide signaling for plant defensive genes exhibits analogies to defense signaling in animals. Proc Natl Acad Sci USA 93: 12053–12058 (1996).
4. Bohlmann H: The role of thionins in plant protection. Crit Rev Plant Sci 13: 1–16 (1994).
5. Bohlmann H, Apel K, Garcia-Olmedo F: Thionins. Plant Mol Biol Rep 12: S75 (1994).
6. Bohlmann H, Clausen S, Behnke S, Giese H, Hiller C, Schrader G, Barkholt V, Ape K: Leaf-thionins of barley—a novel class of cell wall proteins toxic to plant-pathogenic fungi and possibly involved in the defense mechanism of plants. EMBO J 7: 1559–1565 (1988).
7. Brisson L F, Tenhaken R, Lamb C: Functions of oxidative cross-linking of cell wall structural proteins in plant disease resistance. Plant Cell 6: 1703–1712 (1994).

8. Boyd L A, Smith P H, Green R M, Brown J K M: The relationship between the expression of defense-related genes and mildew development in barley. Mol Plant-Microbe Interact 7: 401–410 (1994).
9. Carmona M J, Molina A, Fernandez J A, Lopez-Fando J J, Garcia-Olmedo F: Expression of the α-thionin gene from barley in tobacco confers enhanced resistance to bacterial pathogens. Plant J 3: 457–462 (1993).
10. Cote F, Cutt J R, Asselin A, Klessig D F: Pathogenesis-related acidic β-1,3-glucanase genes of tobacco are regulated by both stress and developmental signals. Mol Plant-Microbe Interact 4: 173–181 (1991).
11. Daykin M E: Infection in blueberry fruit by *Colletotrichum gloeosporioides*. Plant Dis 68: 984–950 (1984).
12. Dean R A, Kúc J: Rapid lignification in response to wounding and infection as a mechanism for induced systemic protection in cucumber. Physiol Plant Pathol 31: 69–81 (1988).
13. Dodds J C, Estrada A, Matcham A, Jeffiies P, Jeger M J: The effect of environmental factors on *Colletofrichum gloeosporioides*, the causal agent of mango anthracnose, in the Philippines. Plant Pathol 40: 568–575 (1991).
14. Ebrahim-Nesbat F, Behnke S, Kleinhofs A, Apel K: Cultivar-related differences in the distribution of cell-wall bound thionins in compatible and incompatible interactions between barley and powdery mildew. Planta 179: 203–210 (1989).
15. Ebrahim-Nesbat F, Bohl S, Heitefuss R, Apel K: Thionin in cell walls and papillae of barley in compatible and incompatible interactions with *Erysiphe graminis* f.sp. *hordei*. Physiol Mol Plant Pathol 43: 343–352 (1993).
16. Epple P, Apel K, Bohlmann H: An *Arabidopsis thaiana* thionin gene is inducible via a signal transduction pathway different from that for pathogenesis-related proteins. Plant Physiol 109: 813–820 (1995).
17. Epple P, Apel K, Bohlmann H: Overexpression of an endogenous thionin gives enhanced resistance of Arabidopsis against *Fusarium oxysporum*. Plant Cell 9: 509–520 (1997).
18. Fils-Lycaon B R, Wiersma P A, Eastwell K C, Sautiere P: A cherry protein and its gene, abundantly expressed in ripening fruit, have been identified as thaumatin-like. Plant Physiol 111: 269–273 (1996).
19. Gaffney T, Friedrich L, Vernooij B, Negrotto D, Nye G, Uknes S, Ward E, Kessmann H, Ryals J: Requirement of salicylic acid for the induction of systemic acquired resistance. Science 261: 754–756 (1993).
20. Garcia-Olmedo F, Molina A, Segura A, Moreno M: The defensive role of nonspecific lipid-transfer proteins in plants. Trend Microbiol 3: 72–74 (1995).
21. Goodman R N, Novacky A J: The Hypersensitive Reaction in Plants to Pathogens. A Resistance Phenomenon. APS Press, St. Paul, Minn., USA (1994).
22. Gu Q, Kawarta E F, Mores M-J, Wu H-M, Cheung A Y. A flower specific cDNA encoding a novel thionin in tobacco. Mol Gen Genet 234: 89–96 (1992).
23. Hildmann T, Ebneth M, Peña-Cortés H, Sanches-Serrano J J, Willmitzer L, Prat S: General roles of abscisic acid and jasmonic acids in gene activation as a result of mechanical wounding. Plant Cell 4: 1157–1170 (1992).
24. Karunanandaa B, Singh A, Kao T: Characterization of a predominantly pistil-expressed gene encoding a γ-thionin-like protein of *Petunia inflata*. Plant Mol Biol 26: 459–464 (1994).
25. Kim W G, Cho E K, Lee E J: Two strains of *Colletotrichum gloeosporioides* Penz. causing anthracnose on pepper fruits. Korean J Plant Pathol 2: 107–113 (1986).
26. Kim K D, Oh B J, Yang J: Differential interactions of a *Colletotrichum gloeosporioides* isolate with green and red pepper fruits. Phytoparasitica 27: 97–106 (1999).
27. Kogel K-H, Ortel B, Jarosch B, Atzorn R, Schiffer R, Wastemack C: Resistance in barley against the powdery mildew fungus (*Erysiphe graminis* f.sp. *hordei*) is not associated with enhanced levels of endogenous jasmonates. Eur J Plant Pathol 101: 319–332 (1995).
28. Liang P, Pardee A B: Differential display of eukaryotic messenger RNA by means of the polymerase chain reaction. Science 257: 967–971 (1992).
29. Linthrost H J M: Pathogenesis-related proteins of plants. Crit Rev Plant Sci 10: 123–150 (1991).
30. Lotan T, Ori N, Fluhr R: Pathogenesis-related proteins are developmentally regulated in tobacco flowers. Plant Cell 1: 881–887 (1989).
31. Manandhar J B, Hartman G L, Wang T C: Conidial germination and appressorial formation of *Colletotrichum capsici* and *C. gloeosporioides* isolates from pepper. Plant Dis 79: 361–366 (1995).
32. Meyer B, Houlné G, Pozueta-Romero J, Schantz M-L, Schantz R: Fruit-specific expression of a defensin-type gene family in bell pepper. Upregulation during ripening and upon wounding. Plant Physiol 112: 615–622 (1996).
33. Milligan S B, Gasser C S: Nature and regulation of pistil-expressed gene in tomato. Plant Mol Biol 28: 691–711 (1995).
34. Oh B J, Balint D E, Giovannoni J J: A modified procedure for PCR-based differential display and demonstration of use in plants for isolation of gene related to fruit ripening. Plant Mol Biol rep 13: 70–81 (1995).
35. Oh B J, Kim K D, Kim Y S: A microscopic characterization of the infection of green and red pepper fruits by an isolate of *Colletotrichum gloeosporioides*. J Phytopathol 146: 301–303 (1998).
36. Peña-Cortés H, Fisahn J, Willmitzer L: Signals involves in wound-induced proteinase inhibitor II gene expression in tomato and potato plants. Proc Natl Acad Sci USA 92: 4106–4113 (1995).
37. Penninckx I A, Eggermont K, Terras F R, Thomma B P, De Samblanx G W, Buchala A, Metraux J P, Manners J M, Broekaert W F: Pathogen-induced systemic activation of a plant defensin gene in Arabidopsis follows a salicylic acid-independent pathway. Plant Cell 8: 2309–2323 (1996).
38. Ponstein A S, Bres-Vloemans S A, Sela-Buurlage M B, van den Elzen P J M, Melchers L S, Cornelissen B J C: A novel pathogen- and wound-inducible tobacco (*Nicotiana tabacum*) protein with antifingal activity. Plant Physiol 104: 109-118 (1994).
39. Prusky D, Plumbley R A, Kobiler I: The relationship between the antifungal diene levels and fingal inhibition during quiescent infections of *Colletotrichum gloeoporioides* in unripe avocado fruits. Plant Pathol 40: 45–52 (1991).
40. Reinbothe S, Mollenhauer B, Reinbothe C: JIP and RIPs: the regulation of plant gene expression by jasmonates in response to environmental cues and pathogens. Plant Cell 6: 1197–1209 (1994).
41. Rojo E, Titarenko E, León J, Berger S, Vancanneyt G, Sánchez-Serrano J J: Reversal protein phosphorylation regulates jasmonic acid-dependent and—independent wound signal transduction pathways in *Arabidopsis thaliana*. Plant J 13: 153–165 (1998).
42. Salzman R A, Tikhonova I, Bordelon B P, Hasegawa P M, Bressan R A: Coordinate accumulation of antifungal proteins and hexoses constitutes a developmentally con- 43. Stevens C, Titarenko E, Hargreaves J A, Gurr S J: Defense-related gene activation during an incompatible interaction between *Stagonospora* (*Septoria*) *nodorum* and barey (*Hordeum vulgare L.*) coleoptile cells. Plant Mol Biol 31: 741–749 (1996).
44. Swinburne T R: Post-Harvest Pathology of Fruits and Vegetables. Academic Press, NY, USA (1983).
45. Terras F R G, Egermont K, Kovaleva V, Raikhel N V, Osborn R W, Kester A, Rees S B, Torrekens S, Van Leuven F, Vanderleyden J, Cammue B P A, Broekaert W F: Small cystein-rich antifingal proteins from radish: their role in host defense. Plant Cell 7: 573–588 (1995).
46. Terras F R G, Schoofs H M E, Thevissen K, Osborn R W, Vanderleyden J, Cammue B P A, Broekaert W F: Synergistic enhancement of the antifungal activity of wheat and barley thionins by radish and oilseed rape 2S albumins and by barley trypsin inhibitors. Plant Physiol 103: 1311–1319 (1993).
47. Titarenko E, Hargreaves J, Keon J, Gurr S J: Defense-related gene expression in barley coleoptile cells following infection by *Septoria nodorum*. In Mechanisms of Plant Defense responses, Fritig B and Legrand M (eds), pp. 308–311. Kluwer Academic Publisher, Dordrecht (1993).
48. Uknes S, Mauch-Mani B, Moyer M, Potter S, Williams S, Dincher S, Chandler D, Slusarenko A, Ward E, Ryals J: Acquired resistance in Arabidopsis. Plant Cell 4: 645–656 (1992).
49. Van Etten H D, Mattews D E, Mattews P S: Phytoalexin detoxification: Importance for pathogenicity and practical implications. Annu Rev Phytopathol 27:143–164 (1989).
50. Vignutelli A, Wasternack C, Apel K, Bohlmann H: Systemic and local induction of an Arabidopsis thionin gene by wounding and pathogens. Plant J 14: 285–295 (1998).
51. Ward E R, Uknes S J, Williams S C, Dincher S S, Wiederhold D L, Alexander D C, Ahl-Goy P. Metraux J-P, Ryals J A: Coordinate gene activity in response to agents that induce systemic acquired resistance. Plant Cell 3: 1085–1094 (1991).

---

What is claimed is:

1. An isolated nucleic acid having the nucleotide sequence of SEQ ID NO:3.

\* \* \* \* \*